(12) United States Patent
Ogien et al.

(10) Patent No.: US 12,288,336 B2
(45) Date of Patent: Apr. 29, 2025

(54) SYSTEMS FOR CHARACTERIZING A REGION OF INTEREST OF A BIOLOGICAL TISSUE

(71) Applicant: DAMAE MEDICAL, Paris (FR)

(72) Inventors: Jonas Ogien, Bourges (FR); Anthony Daures, Suresnes (FR)

(73) Assignee: DAMAE MEDICAL, Paris (FR)

( * ) Notice: Subject to any disclaimer, the term of this patent is extended or adjusted under 35 U.S.C. 154(b) by 0 days.

(21) Appl. No.: 18/703,681

(22) PCT Filed: Oct. 28, 2022

(86) PCT No.: PCT/EP2022/080301
§ 371 (c)(1),
(2) Date: Apr. 22, 2024

(87) PCT Pub. No.: WO2023/073220
PCT Pub. Date: May 4, 2023

(65) Prior Publication Data
US 2024/0420323 A1    Dec. 19, 2024

(30) Foreign Application Priority Data

Oct. 29, 2021    (FR) ...................... 2111545

(51) Int. Cl.
*G06T 7/00*         (2017.01)
*G06T 3/4038*       (2024.01)
*G06T 11/60*        (2006.01)

(52) U.S. Cl.
CPC .......... *G06T 7/0012* (2013.01); *G06T 3/4038* (2013.01); *G06T 11/60* (2013.01);
(Continued)

(58) Field of Classification Search
None
See application file for complete search history.

(56) References Cited

U.S. PATENT DOCUMENTS

| 7,136,518 | B2 * | 11/2006 | Griffin | ................... | G01N 21/31 |
| | | | | | 382/128 |
| 9,185,357 | B2 | 11/2015 | Boccara et al. | | |
| 2019/0343390 | A1 * | 11/2019 | Boppart | ................ | A61B 1/227 |

FOREIGN PATENT DOCUMENTS

| FR | 3107604 A1 | 8/2021 |
| WO | 2015/092019 A1 | 6/2015 |

(Continued)

OTHER PUBLICATIONS

International Search Report issued in PCT/EP2022/080301 on Feb. 20, 2023 (8 pages).

(Continued)

*Primary Examiner* — Michael J Cobb
(74) *Attorney, Agent, or Firm* — Osha Bergman Watanabe & Burton LLP

(57) ABSTRACT

A system for characterizing a region of interest of a biological tissue that includes a sighting device that produces an image in reflection of an elementary surface of the biological tissue. The system further includes a microscopic analysis device that detects, in a detection pattern included in the elementary surface, a light beam emitted by the biological tissue in response to illumination of the biological tissue and generates microscopic analysis information, and to determine a tissue characterization parameter from the microscopic analysis information. The system further includes a processing module that localizes, relative to a surface image of the region of interest, each elementary surface image of various elementary surface images and produces a map element for the characterization parameter. The system further includes a display module that displays a tissue map.

14 Claims, 9 Drawing Sheets

(52) U.S. Cl.
CPC ............... *G06T 2207/10056* (2013.01); *G06T 2207/10101* (2013.01); *G06T 2207/20084* (2013.01); *G06T 2207/20212* (2013.01); *G06T 2207/30088* (2013.01); *G06T 2210/41* (2013.01)

(56) References Cited

FOREIGN PATENT DOCUMENTS

| WO | 2020/087164 A1 | 5/2020 |
| WO | 2021067563 A1 | 4/2021 |
| WO | 2022/017784 A1 | 1/2022 |

OTHER PUBLICATIONS

Written Opinion of the International Searching Authority issued in PCT/EP2022/080301 on Feb. 20, 2023 (10 pages).

Davis, A. et al.; "Line-field confocal optical coherence tomography operating simultaneously at 800 nm and 1300 nm center wavelengths"; Label-free Biomedical Imaging and Sensing (LBIS) Proc. of SPIE, vol. 10890, Mar. 4, 2019 (7 pages).

Ogien, J. et al.; "Video-mosaicking of human skin in vivo using handheld line-field confocal optical coherence tomography"; Photonics in Dermatology and Plastic Surgery, vol. 11211, Feb. 19, 2020, (6 pages).

Li, S.; "A review of feature detection and match algorithms for localization and mapping"; IOP Conference Series: Materials Science and Engineering, vol. 231, 2017 (8 pages).

Alfonso-Garcia, A. et al.; "Real-time augmented reality for delineation of surgical margins during neurosurgery using autofluorescence lifetime contrast"; Journal of Biophotonics, Jul. 11, 2019, (12 pages).

Beaurepaire, E. et al.; "Full-field optical coherence microscopy"; Optics Letters, vol. 23, No. 4, Feb. 15, 1998, pp. 244-246 (3 pages).

A. Davis et al. "Simultaneous dual-band line-field confocal optical coherence tomography: application to skin imaging" Biomedical Optics Express, vol. 10, No. 2; Feb. 2019 (13 pages).

Office Action issued in Australian Application No. 2022377223; Dated May 29, 2024 (6 pages).

* cited by examiner

SYSTEMS FOR CHARACTERIZING A REGION OF INTEREST OF A BIOLOGICAL TISSUE

TECHNICAL FIELD OF THE INVENTION

The present description relates to systems for characterizing a region of interest of a biological tissue, and applies in particular to the characterization of a region of interest of the skin in the context of an excision.

PRIOR ART

In the context for example of excision of a skin tumor, it is important for the surgeon to characterize the extent of the tumor as best possible in order to extract all tumor tissue while at the same time limiting the extraction of healthy tissue around the tumor. The contours of a spatial extent surrounding the region of tissue to be extracted are generally called "surgical margins" or "excision margins". Excision margins should also advantageously take into account the presence of lesions deep in the skin.

Generally speaking, optical methods for determining excision margins in surgery are known. Thus, for example, the article by A. Alfonso-Garcia et al. [Ref. 1] describes, in neurosurgery, an imaging technique based on FLIm (Fluorescence Lifetime Imaging) multi-photon fluorescence that makes it possible, in real time during a surgical intervention, to identify regions of the brain that are affected by a tumor and healthy regions, in order to delineate surgical margins. More specifically, the region of interest is filmed by way of a camera. FLIm fluorescence analysis is carried out in parallel by way of an optical fiber that is moved by an operator over the region of interest, the optical fiber allowing the excitation light beam to be transported and the fluorescence signal to be collected. A characteristic parameter of FLIm fluorescence analysis, namely the color-coded fluorescence lifetime, is superimposed on the video images in order to present the operator with an augmented reality view of the region of interest.

However, such a technique is difficult to adapt to the excision of skin tumors due to the precision required to delineate excision margins, firstly because there is no depth resolution of the fluorescence signal in the technique described above, and secondly because there may be positioning errors between the surface images acquired by the camera and the representation of the characteristic parameter of the fluorescence, due to inevitable movements of the biological tissue to be analyzed.

In published patent application WO2020087164 [Ref. 2], optical coherence tomography (OCT) images are used to delineate the excision margins of ablated tissue, for example to determine whether a tumor has been completely extracted, in particular in conservative breast surgery interventions. A convolutional neural network (CNN) is trained to recognize, in the OCT images, a probability of anomalies being present in the region under exploration. The OCT images may be three-dimensional, thereby also making it possible to take into account deep tumor regions in order to determine excision margins. An annotated image of the three-dimensional image thus acquired may be generated, with an indication of the probability of anomalies in the region of interest.

However, the method described in [Ref. 2] is suitable for ex vivo applications, and would not be suitable for in vivo applications. This is because, firstly, acquiring all of the images from which the analysis is carried out takes a long time (typically several minutes). This is also because, even if artificial intelligence tools are used to recognize anomalies in the OCT images, these images would remain difficult for a practitioner to interpret in the context of an in vivo characterization, during which practitioners are accustomed to observing surface images.

The present description proposes systems for characterizing a region of interest of a biological tissue, enabling in particular in vivo characterization so as to easily guide an excision, in particular characterization of the skin, which allows for both excellent precision and ease of interpretation for a practitioner.

SUMMARY OF THE INVENTION

In the present description, the term "comprise" means the same as "include", "contain", and is inclusive or open and does not rule out other elements that are not described or shown. Moreover, in the present description, the term "approximately" or "substantially" is synonymous with (means the same as) having a lower and/or upper margin of 10%, for example 5%, of the respective value.

According to a first aspect, the present description relates to a system for characterizing a region of interest of a biological tissue, comprising:
a sighting device comprising:
  a full-field illumination device configured to illuminate the biological tissue in a first spectral band;
  a two-dimensional detector comprising a detection area;
  a full-field imaging device comprising a first optical axis and configured to optically conjugate an elementary surface of the biological tissue with said detection area of the two-dimensional detector, the two-dimensional detector producing, during operation, an image in reflection of said elementary surface;
a microscopic analysis device comprising:
  a microscope objective comprising a second optical axis mechanically integral with the first optical axis;
  an illumination path configured to illuminate the biological tissue in a first illumination pattern included in said elementary surface, and in a second spectral band;
  a detection path comprising said microscope objective, said detection path being configured to detect, in a detection pattern included in said elementary surface, a light beam emitted by the biological tissue in response to said illumination of the biological tissue and generate microscopic analysis information;
a data processing unit comprising
  a first processing module configured to determine, from said microscopic analysis information, at least one first biological tissue characterization parameter at a given number of points of said detection pattern;
  a second processing module configured to
    localize, relative to a surface image of the region of interest, each elementary surface image of a plurality of elementary surface images acquired successively by moving the full-field imaging device of the sighting path and
    produce at least one first map element for said at least one first characterization parameter, from said at least one first characterization parameter determined for at least some of the elementary surface images of said plurality of elementary surface images;

a display module configured to display a tissue map comprising at least said first map element, said map being localized relative to said surface image of the region of interest.

In the present description, the illumination pattern depends on the illumination path of the microscopic analysis path and may comprise an illumination point, an illumination line or an illumination surface, for example a rectangular surface resulting from the scanning of an illumination point or an illumination line. An illumination point is defined, more precisely, as the diffraction pattern resulting from the focusing, by the microscope objective of the microscopic analysis path, of a collimated light beam incident on said objective. The illumination pattern may also comprise an illumination surface that does not result from scanning, for example a surface with a circular geometry, in the case of a full-field microscopic analysis path.

The light beam emitted by the biological tissue in response to the illumination of the sample may be a reflected beam, a backscattered beam, or a beam resulting from an emission process at another wavelength (for example fluorescence, Raman scattering, etc.).

In addition, an elementary surface is defined by the field in the object space of the full-field imaging device of the sighting device, referred to as an "effective field" in the present description. An elementary surface is defined for example by a circle when for example the effective field is limited by the optics of the sighting device, or by a rectangle when the effective field is limited by the detection area of the two-dimensional detector of the sighting device. An image of an elementary surface produced by the sighting device is also referred to as a "sighting image" in the present description.

The detection pattern is included in the elementary surface produced by the sighting device and is included in the illumination pattern or is of the same order of magnitude, and depends on the detection path of the microscopic analysis device. The detection pattern may comprise a detection point, a detection line or a detection surface, for example a rectangular surface resulting from the scanning of a line, or, in the case of a full-field microscopic analysis path, a surface optically conjugate with a detection area of a detector. A detection point is defined here in the object space by an elementary zone optically conjugate with an elementary detector of a detector of the detection path of the microscopic analysis device.

The characterization system according to the first aspect, due to the original combination of characteristics, makes it possible to localize at least one first tissue characterization parameter, at a given number of points of said detection pattern, relative to a surface image of the region of interest with excellent precision, that is to say better than a few microns.

A first map element for said at least one first characterization parameter may then be produced from the first tissue characterization parameter localized at a given number of points of the surface image of the region of interest. This map element may correspond directly to an association of given visual characteristics (color, opacity, thickness, etc.) for these points or some of these points. This map element may also result from the application of linear operations (interpolation, averaging, etc.), in particular so as to form a continuous surface, associated with given visual characteristics (color, opacity, contour, contour sharpness, etc.). This map element may also result from morphomathematical operations (dilation, erosion, etc.) applied to the continuous surface, and associated with given visual characteristics (color, opacity, contour, contour sharpness, etc.).

According to one or more exemplary embodiments, said elementary surface images have a partial overlap and said surface image of the region of interest is produced by mosaicking said plurality of elementary surface images. The localization of an image of an elementary surface in the surface image of the region of interest is then carried out automatically. For example, said combination by mosaicking is carried out as the images of said elementary surfaces are acquired, thereby making it possible to have for example a real-time display of the acquired surface image and of the map of said at least one first identification parameter, allowing for example a practitioner to make decisions during the acquisition.

According to one or more exemplary embodiments, said at least one first map element is produced as the acquisition progresses.

In other exemplary embodiments, said combination by mosaicking is established after acquisition of all of the elementary surface images (sighting images). Fewer processing resources are then used in real time.

According to one or more exemplary embodiments, said surface image of the region of interest is produced by way of an imaging system independent of said characterization system. For example, the surface image of the region of interest is a dermoscopic image acquired by a dermatoscope.

In these examples, the localization of an image of an elementary surface relative to the surface image of the region of interest may be achieved using known techniques, such as, for example, a technique comprising identification of points of interest ("feature-detection") and then matching of points of interest ("feature-match"). Such a technique is described for example in the Article by S. Li [Ref. 3]. Mosaicking of the elementary surface images is then no longer necessary for the localization.

In some exemplary embodiments, the localization of each elementary surface image of the plurality of elementary surface images relative to the surface image of the region of interest may comprise pre-processing steps carried out on said images, such as for example: localized enhancement or denoising filtering in order to mask or highlight structures of interest, applying a histogram matching or normalization algorithm to a set of said images, applying a mosaicking algorithm to a set of said images in order to increase the level of overlap with the surface image of the region of interest.

For example, in some exemplary embodiments, the display module is configured to additionally display said surface image of the region of interest, the surface image of the region of interest being easy to interpret for a practitioner. In other exemplary embodiments, for example when the surface image is obtained by mosaicking the plurality of elementary surface images, the display module may be configured to additionally display another surface image of the entire region of interest acquired by another imaging system, for example a dermoscopic image acquired by a dermatoscope, and localized relative to the surface image of the region of interest acquired by the characterization system according to the first aspect. For example, in some exemplary embodiments, the display module is configured such that said tissue map is displayed in a manner superimposed on said surface image of the region of interest or, for example when the surface image is obtained by mosaicking the plurality of elementary surface images, in a manner superimposed on another surface image of the entire region of interest, acquired by another imaging system and localized relative to the surface image of the region of interest acquired by the characterization system according to the first aspect.

In other exemplary embodiments, the display module may be configured such that said tissue map is displayed in a manner juxtaposed with said surface image of the region of interest or, for example when the surface image is obtained by mosaicking the plurality of elementary surface images, in a manner juxtaposed with another surface image of the entire region of interest, acquired by another imaging system and localized relative to the surface image of the region of interest acquired by the characterization system according to the first aspect. In these exemplary embodiments, the display module may additionally be configured to show a common cursor both in said tissue map and in the surface image of the region of interest, that is to say a graphical element configured to localize the same spatial position on the map and said surface image of the region of interest.

Of course, the display module may be configured to operate in one and/or another of the exemplary embodiments described above, at the choice of a user.

In any case, excision is facilitated because the practitioner is able, at the level of the tissue surface, to easily and precisely identify the contour of a region of interest, for example the contour of a tumor, even if it is not directly visible on the surface. This precision is made possible in particular due to the mechanical solidarity between the first optical axis of the full-field imaging device of the sighting device and the second optical axis of the microscope objective of the microscopic analysis device.

According to one or more exemplary embodiments, the full-field imaging device of the sighting device comprises said microscope objective. In these exemplary embodiments, the first optical axis and the second optical axis are coincident, thereby making it possible to have a more compact characterization system while at the same time benefiting from a sighting image that is of high quality since it is obtained with the microscope objective. Moreover, the localization of said at least one first characterization parameter on the surface image is simplified.

In other exemplary embodiments, the full-field imaging device of the sighting device does not comprise the microscope objective of the microscopic analysis device. In this case, however, the mechanical solidarity of the first optical axis and of the second optical axis will make it possible to localize the detection pattern in the sighting image and thus to localize said at least one first parameter on the surface image of the region of interest.

In some exemplary embodiments, the first spectral band of the full-field illumination device of the sighting device and the second spectral band of the illumination path of the microscopic analysis device differ at least partially. This makes it possible, in some exemplary embodiments, to at least partially filter light coming from the illumination path of the microscopic analysis device and incident in the sighting device or, vice versa, to at least partially filter light coming from the full-field illumination device of the sighting device and incident in the microscopic analysis system.

According to one or more exemplary embodiments, the full-field illumination device of the sighting path comprises a plurality of light sources arranged on a periphery of a distal face of the microscope objective, that is to say the face of the microscope objective in the space of the biological tissue. This configuration allows direct illumination of the biological tissue. Of course, other configurations are possible for the full-field illumination device of the sighting path.

According to one or more exemplary embodiments, the illumination path of the microscopic analysis device is configured to illuminate the biological tissue through the microscope objective. In other exemplary embodiments, direct illumination of the biological tissue is possible without involving the microscope objective, for example by way of optical fibers. According to one or more exemplary embodiments, said microscopic analysis path is a confocal imaging path and/or optical coherence tomography imaging path, and said biological tissue microscopic analysis information comprises at least one image of the biological tissue. For example, the microscopic analysis path is an optical coherence tomography imaging path as described in the prior art and is configured to form B-scan images or C-scan images (or front-on images) of the biological tissue or 3D images of the biological tissue. In a known manner, a sectional image of biological tissue referred to as a "B-scan" is an image formed in a plane parallel to the optical axis of the microscope objective; a sectional image of the sample referred to as a "C-scan", or front-on image, is an image formed in a plane perpendicular to the optical axis of the microscope objective, and a 3D image of the biological tissue results from the acquisition of a plurality of B-scan images or C-scan images, and thus allows analysis of the biological tissue in a volume.

According to one or more exemplary embodiments, said microscopic analysis path is a spectroscopic analysis path and said biological tissue microscopic analysis information comprises at least one spectrum of said light beam emitted by the sample at at least one point of the sample.

According to one or more exemplary embodiments, said at least one first biological tissue characterization parameter on the basis of which the first processing module generates a tissue map from said microscopic analysis information is a parameter chosen from among: a morphological measurement, a cytological measurement, an optical measurement, a measurement characterizing a chemical composition, a mechanical measurement, a combination of these measurements, a score for characterizing the state of the tissue, for example based on at least one of these measurements, for example a score indicating a probability of a lesion being present, for example a lesion of predetermined nature. According to one or more exemplary embodiments, said first module for processing said microscopic analysis information comprises an artificial intelligence module, for example based on a deep learning model using neural networks.

Generally speaking, the processing modules, processing unit or control unit to which reference is made in the present description may comprise one or more physical entities, and may be combined in one or more computers. When reference is made in the present description to computing or processing steps for the implementation in particular of steps of methods, it should be understood that each computing or processing step may be implemented by software, hardware, firmware, microcode or any appropriate combination of these technologies. When software is used, each computing or processing step may be implemented by computer program instructions or software code. These instructions may be stored or transmitted to a storage medium able to be read by the control unit and/or executed by the control unit in order to implement these computing or processing steps.

Thus, in a characterization system according to the first aspect, the first processing module and the second processing module of the processing unit may be combined in one or more computers.

In some exemplary embodiments, the biological tissue is skin and the characterization system is configured to be implemented in vivo. The characterization system makes it possible for example to characterize cancerous lesions.

According to one or more exemplary embodiments, the second processing module is furthermore configured to determine excision margins of a region of a tissue to be extracted based on said at least one first map element.

For example, the excision margins are determined from the contour defined by said map, for example by adding an additional margin, for example an additional margin of between approximately 0.5 mm and approximately 5 mm.

According to a second aspect, the present description relates to a computer program product comprising program code instructions for implementing a data processing method with a view to characterizing a region of interest of a biological tissue when said program is executed on a computer, the data being obtained by way of an optical analysis system comprising:

a sighting device comprising:
   a full-field illumination device configured to illuminate the biological tissue in a first spectral band;
   a two-dimensional detector comprising a detection area;
   a full-field imaging device comprising a first optical axis and configured to optically conjugate an elementary surface of the biological tissue with said detection area of the two-dimensional detector, the two-dimensional detector producing, during operation, an image in reflection of said elementary surface;
a microscopic analysis device comprising:
   a microscope objective comprising a second optical axis mechanically integral with the first optical axis;
   an illumination path configured to illuminate the biological tissue in a first illumination pattern included in said elementary surface, and in a second spectral band;
   a detection path comprising said microscope objective, said detection path being configured to detect, in a detection pattern included in said elementary surface, a light beam emitted by the biological tissue in response to said illumination of the biological tissue and generate microscopic analysis information;
the data processing method comprising the following steps:
   determining, from said microscopic analysis information, said at least one first biological tissue characterization parameter at a given number of points of said detection pattern;
   localizing, relative to a surface image of the region of interest, each elementary surface image of a plurality of elementary surface images acquired successively by moving the full-field imaging device of the sighting path and
   producing at least one first map element for said at least one first characterization parameter, from said at least one first characterization parameter determined for at least some of the elementary surface images of said plurality of elementary surface images.

The optical analysis system is for example a system as described in [Ref. 7].

The computer program product may thus be executed on a computer that is not part of the optical analysis system.

According to one or more exemplary embodiments, said elementary surface images have a partial overlap and said surface image of the region of interest is produced by mosaicking said plurality of elementary surface images.

According to one or more exemplary embodiments, said at least one first biological tissue characterization parameter is determined by way an artificial intelligence module based on a deep learning model using neural networks.

According to one or more exemplary embodiments, the method furthermore comprises determining excision margins of a region of a tissue to be extracted based on said at least one first map element.

According to a third aspect, the present description relates to a non-transient computer-readable storage medium storing a computer program product according to the second aspect.

BRIEF DESCRIPTION OF THE FIGURES

Other advantages and features of the invention will become apparent upon reading the description, which is illustrated by the following figures.

DETAILED DESCRIPTION OF THE INVENTION

In the following detailed description, a large number of specific details are set out in order to provide a more in-depth understanding of the present description. However, it will be apparent to those skilled in the art that the present description may be implemented without these specific details. In other cases, well-known features have not been described in detail in order to avoid needlessly complicating the description.

Moreover, in the figures, the elements are not shown to scale for better visibility.

Figure 1A:
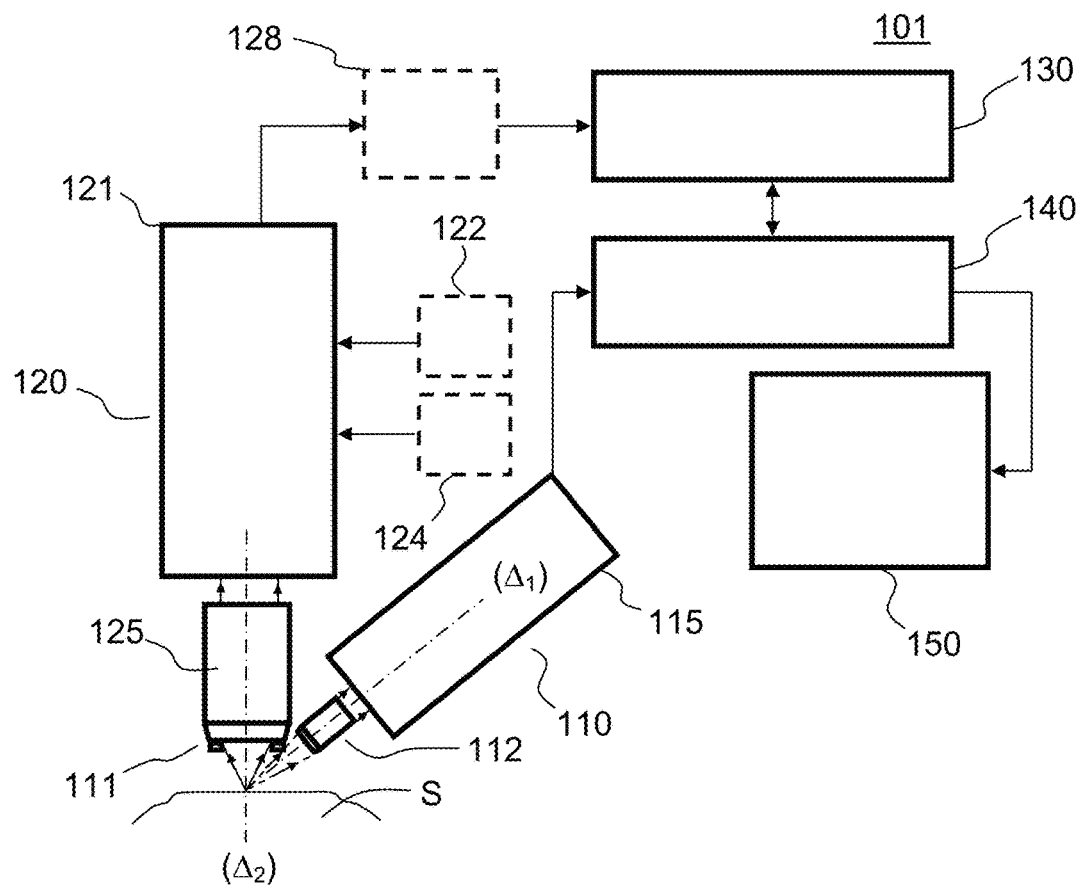
FIG. 1A shows a diagram illustrating a first example of a system for characterizing a region of interest of a biological tissue according to the present description.
Figure 1B:
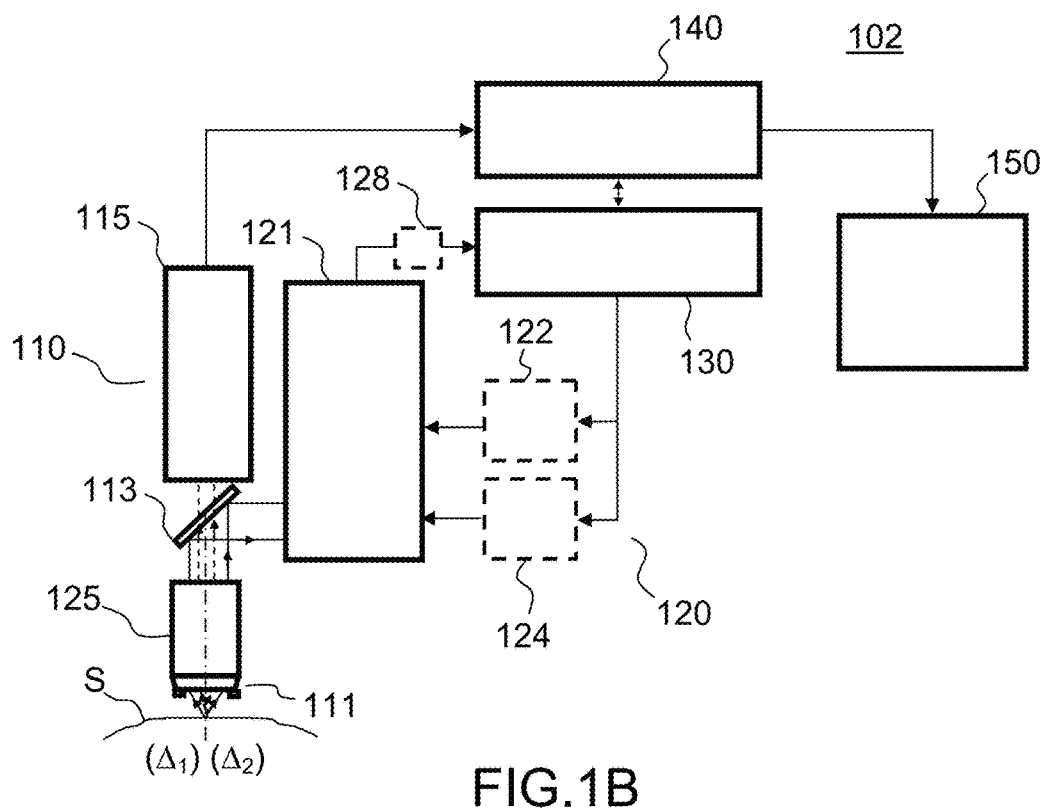
FIG. 1B shows a diagram illustrating a second example of a system for characterizing a region of interest of a biological tissue according to the present description.

FIG. 1A shows a diagram illustrating a first example 101 of a system for characterizing a region of interest of a biological tissue S according to the present description, and FIG. 1B shows a diagram illustrating a second example 102 of a system for characterizing a region of interest of a biological tissue according to the present description.

The characterization systems 101, 102 each comprise a sighting device 110 comprising a full-field illumination device 111, for example a set of light-emitting diodes or LEDs, configured to illuminate the biological tissue in a first spectral band, a two-dimensional detector (not shown in the figures) and a full-field imaging device (not shown in the figures), only the optical axis 41 of the full-field imaging device being shown schematically. The full-field imaging device of the sighting device is configured to optically conjugate an elementary surface of the biological tissue with a detection area of the two-dimensional detector, the two-dimensional detector producing, during operation, an image in reflection of said elementary surface, referred to as a "sighting image" in the present description. For example, the sighting device 110 comprises a mount 115 configured to receive all or some of the optoelectronic elements forming the full-field imaging device and the two-dimensional detector.

The characterization systems 101, 102 each additionally comprise a microscopic analysis device 120 comprising a microscope objective 125 comprising an optical axis $\Delta_2$, mechanically integral with the optical axis $A_1$ of the full-field imaging device.

In the example of a characterization system 101 illustrated in FIG. 1A, the optical axes $\Delta_1$ of the full-field imaging device of the sighting device 110 and $\Delta_2$ of the microscope objective 125 are distinct. The mechanical solidarity of the axes $\Delta_1$ and $\Delta_2$ is provided for example by a common mount (not shown in FIG. 1A).

In the example of a characterization system 102 illustrated in FIG. 1B, the microscope objective 125 is contained within the full-field imaging device of the sighting device 110 and the optical axes $\Delta_1$ and $\Delta_2$ are coincident. In this example, a beam splitter element 113 makes it possible to split the detection paths of the sighting device and of the microscopic analysis device.

In both examples, it is possible to define a distal end of the characterization system that is configured to be in contact with or close to the biological tissue S. For example, in the case of characterizing skin, the distal end of the characterization system may comprise a glass slide (not shown in the figures) or a mechanical part (not shown in the figures) that makes it possible to set a predetermined distance between the skin and an entrance pupil of the microscope objective.

In these examples, the full-field illumination device 111 of the sighting device comprises a set of LEDs arranged on a distal end of the sighting device.

The microscopic analysis device 120 in each of these examples also comprises an illumination path configured to illuminate the biological tissue, for example through the microscope objective, in a first illumination pattern included in said elementary surface, and a detection path comprising said microscope objective 125, said detection path being configured to detect, in a detection pattern included in said elementary surface, a light beam emitted by the biological tissue in response to said illumination of the biological tissue and generate microscopic analysis information. An illumination path and a detection path of the microscopic analysis device 120 are described in relation to FIG. 2 in the case of one particular example.

In the examples shown in FIG. 1A and FIG. 1B, the microscopic analysis device 120 comprises a mount 121 generally comprising at least some of the optoelectronic elements of the detection path of the microscopic analysis device, and may comprise at least some of the optoelectronic elements of the illumination path. In some exemplary embodiments, the optoelectronic elements may comprise, without limitation, one or another of the following elements: an illumination source, an interferometric assembly, a detector and an associated processing unit, one or more optical systems for providing optical conjugations between image planes or pupil planes, one or more reflecting mirrors, one or more scanning systems, etc. The arrangement of such optical elements is known to those skilled in the art and depends on the microscopic analysis that it is sought to carry out.

In some exemplary embodiments, some of said optoelectronic elements may be located outside the mount 121, such as for example an illumination source 124, for example a laser source, a detector 128, for example a camera, associated with a processing unit (not shown), for generating microscopic analysis information from a detection signal and, optionally, one or more controllers 122 for controlling the optoelectronic elements arranged in the mount 121. The one or more controllers are for example electronic cards configured to control an axial displacement of the microscope objective 125 if necessary, or mirrors of a scanning system, a light source, etc. The one or more controllers, along with the source 124, may be controlled by a control unit (not shown).

When the microscopic analysis device 120 is configured for confocal imaging and/or optical coherence tomography imaging, said microscopic analysis information comprises at least one image of the biological tissue. When the microscopic analysis device 120 is configured for spectroscopic analysis, said microscopic analysis information comprises at least one spectrum of said light beam emitted by the illuminated biological tissue.

It should be noted that, in other exemplary embodiments, the illumination source of the illumination path and/or the detector of the detection path may be integrated into the mount 121.

In the examples illustrated in FIG. 1A and FIG. 1B, separate mounts 115 and 121 are shown. Of course, in practice, in some exemplary embodiments, a single mount may be provided for the arrangement of the elements of the sighting device and of the microscopic analysis device.

Figure 3A:
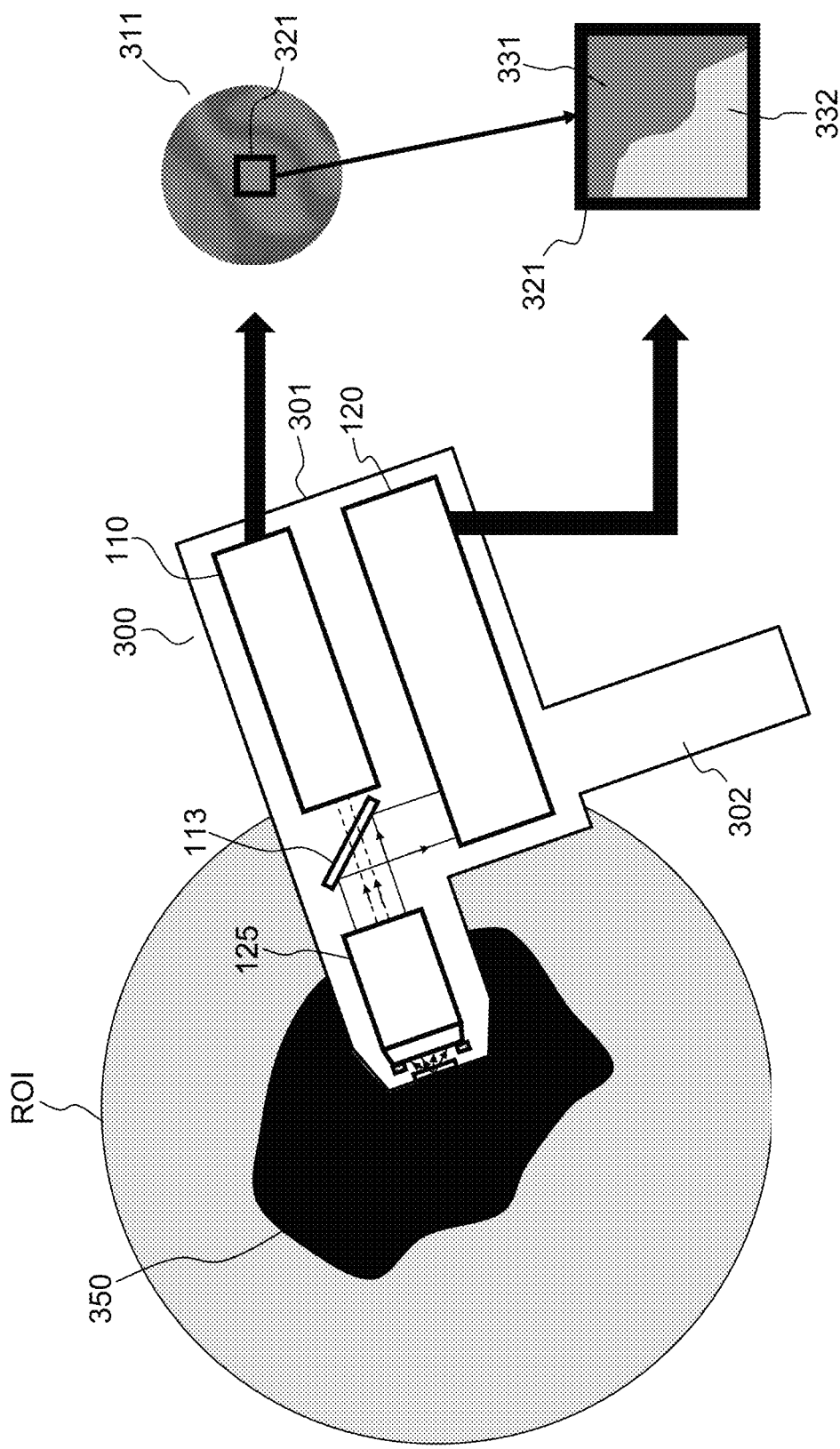
FIG. 3A shows a diagram illustrating, in simplified form, the implementation of steps of a method for characterizing a region of interest of a biological tissue, by way of one example of a characterization system according to the present description.

In some exemplary embodiments, as illustrated for example in FIG. 3A, an additional mount (not shown in FIG. 1A and FIG. 1B) may also be provided to ensure mechanical solidarity between the optical axes by solidly joining the mounts 121, 115, the microscope objective 125 and the full-field imaging device of the sighting device.

The characterization systems 101, 102 furthermore comprise a processing unit with a first processing module 130 and a second processing module 140. The first processing module 130 is configured to determine, from said microscopic analysis information, at least one first biological tissue characterization parameter at a given number of points of said detection pattern. The second processing module 140 is configured to localize, relative to a surface image of the region of interest, each elementary surface image of a plurality of elementary surface images acquired successively by moving the full-field imaging device of the sighting path. For example, the surface image of the region of interest is obtained by mosaicking the plurality of elementary surface images acquired successively by moving the full-field imaging device of the sighting path and having a partial overlap. The second processing module 140 is also configured to produce at least one first map element for said at least one first characterization parameter, from said at least one first characterization parameter determined for each elementary surface image of said plurality of elementary surface images. The characterization systems 101, 102 moreover comprise a display module 150 configured to display a tissue map comprising at least said first map element, said map being localized relative to said surface image, as will be explained in more detail below.

In the example of FIG. 1B, the first optical axis and the second optical axis being coincident, the localization of the map of at least one characterization parameter on the surface image is simplified. However, in the example of FIG. 1A, the mechanical solidarity of the first optical axis and of the second optical axis makes it possible to localize the detection pattern in the sighting image and thus to localize the map of said at least one characterization parameter on the surface image of the region of interest.

Figure 2:
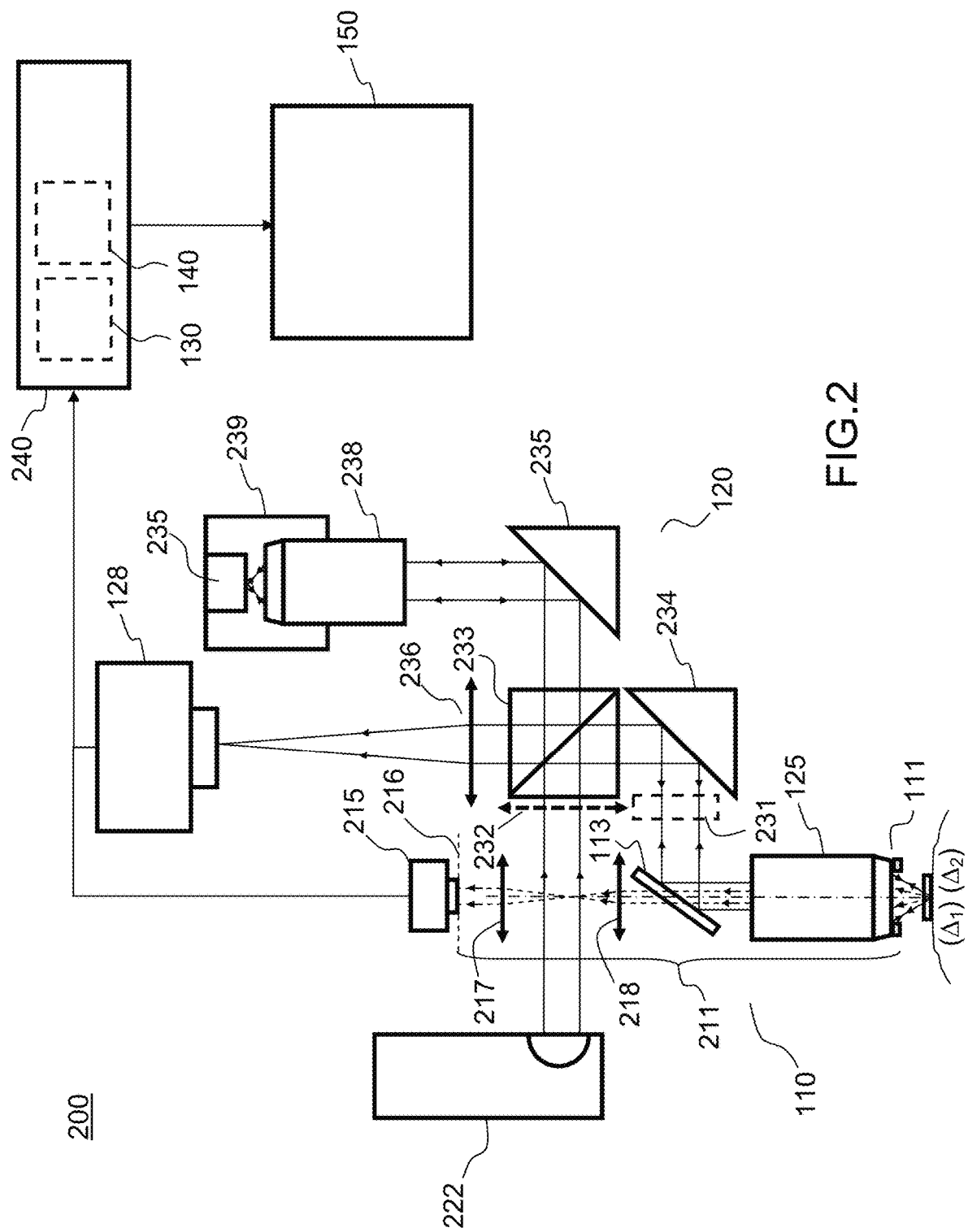
FIG. 2 shows a diagram illustrating one example of a system for characterizing a region of interest of a biological tissue implementing optical coherence tomography imaging microscopic analysis.

FIG. 2 shows a diagram illustrating one example of a system for characterizing a region of interest of a biological tissue implementing optical coherence tomography imaging microscopic analysis, for example an LC-OCT path as described for example in [Ref. 4]. The characterization system 200 comprises, in this example, a microscope objective 125 common to a microscopic analysis device 120 and to a wide-field imaging device 211 of a sighting device 110. In this example, the one or more mounts are not shown. The characterization system 200 comprises, as in the previous examples, the processing modules 130, 140, for example modules of a computer 240, along with the display module 150. The sighting device 110 thus comprises, in this example, the microscope objective 125, the beam splitter element 113, a full-field illumination device 111 configured to illuminate the biological tissue in a first spectral band, a two-dimensional detector 215 with a detection area 216, and one or more imaging elements represented in FIG. 2 by the elements 217, 218 and configured to form, with said microscope objective 125, a full-field imaging device 211 that optically conjugates a given effective field of the sample with the detection area 216 of the two-dimensional detector 215. The sighting device thus makes it possible to form a surface-reflected sighting image of an elementary surface whose dimensions are defined by the effective field. The two-dimensional detector 215 is connected to the processing module 140 configured to combine a plurality of elementary surface images by mosaicking.

In this example, the full-field illumination device 111 comprises a plurality of light sources arranged on a distal part of the characterization system 200, for example on a periphery of a distal face of the microscope objective 125, the full-field illumination device allowing direct illumination of the biological tissue S. The light sources are for example light-emitting diodes emitting at wavelengths between approximately 400 nm and approximately 800 nm. Of course, other illumination devices are possible, such as for example a source arranged upstream of the microscope objective and a beam splitter element, for example a splitter cube, configured to direct an illumination beam through the microscope objective toward the biological tissue.

In the example of FIG. 2, the microscopic analysis device 120 comprises an illumination path configured to illuminate the sample through the microscope objective 125 in a given illumination pattern in a second spectral band that may differ at least partially from the first spectral band. The illumination path comprises for example an illumination source 222 configured for example to emit a collimated light beam, a cylindrical reflecting lens or mirror 232 (for example in the case of an LC-OCT path), a splitter element 233 (splitter cube or splitter plate) and a reflective element 234 (optional) configured to send an illumination beam emitted by the illumination source toward the microscope objective 125. In this example, the illumination path also comprises a scanning device 231 for scanning the illumination beam, configured to scan the illumination beam in one or two dimensions, and the splitter element 113 configured to split the sighting path and the microscopic analysis path.

The illumination source 222 may comprise for example a (spatially) coherent, polychromatic, collimated light emission source. Optics and/or spatial filters (not shown) may make the source collimated and/or coherent and/or give it a specific spectral distribution. The center wavelength of the source depends on the application, for example between 600 nm and 1500 nm, and the spectral width is for example approximately between 50 nm and 250 nm. In the case of an LC-OCT application, as described for example in Ref. 4, the illumination source 222 may comprise for example, and without limitation, a supercontinuum laser spectrally filtered by an optical fiber for emission around approximately 800 nm and collimated by an off-axis parabolic mirror. In the case of an application to full-field tomography imaging or FF-OCT (for "Full Field OCT"), as described for example in the Article by E. Beaurepaire et al. [Ref. 5]), the illumination source may be chosen to be spatially non-coherent and comprise means for full-field illumination of the sample, for example a Köhler illumination system. The cylindrical optical element 232 is optional and allows microscopy with illumination along a line ("line-field" microscopy).

The scanning device 231 for scanning the illumination beam may be configured for one-dimensional or two-dimensional scanning of a point or a line so as to form, in a known manner, a sectional image of the sample referred to as a "B-scan", that is to say in a plane parallel to the optical axis of the microscope objective, a sectional image of the sample referred to as a "C-scan", or front-on image, that is to say in a plane perpendicular to the optical axis of the microscope objective, or a 3D image of the sample resulting from the acquisition of a plurality of B-scan images or C-scan images. As previously, the scanning device may comprise one or more scanning elements chosen from among the following elements: galvanometric mirrors, polygonal mirrors, electro or acousto-optic deflection systems, or a combination of these various elements (in the case of two-dimensional scanning). The scanning device may also include optics for conjugating at least one of said scanning elements with an entrance pupil of the microscope objective 125 in order for example to avoid vignetting.

The detection path of the microscopic analysis device is configured to detect a light beam emitted by the sample in response to said illumination of the sample, in a given detection pattern. In this particular (non-limiting) example, the detection path comprises an interferometer for carrying out optical coherence tomography microscopy. More precisely, the interferometer comprises an object arm with the microscope objective 125, the scanning device 231 and reflective or partially reflective elements 113, 234, 233 configured to send a beam emitted by the sample S in response to said illumination of the sample to a detector 128.

The interferometer of the detection path furthermore comprises a reference arm, separated in this example from the object arm by the splitter cube 233, and comprising, in a known manner, a microscope objective 238 (optional), for example similar to the microscope objective 125 for carrying out dispersion compensation, a dispersion compensation system (optional, not shown), a reference mirror 235, a platform 239 (optional) configured for example to displace the reference mirror 235 when modulation of the optical path on the reference arm is required. In this example, the detection path furthermore comprises an objective 236 configured to optically conjugate, with the microscope objective, a plane of the sample S with a detection area of the detector 128.

In this example, the detector 128 comprises an optical sensor with a detection area, and may also include spatial filters for confocal detection, if this is not provided by the dimensions of the detection area, and/or spectral filters for limiting the detected wavelength band. The sensor may comprise an elementary detection surface (for example a photodiode) in the case of a point scanning system, a one-dimensional sensor (for example a linear camera) in the case of a "line-field" system, or a two-dimensional sensor of which only a region of interest is considered in order to act as an elementary detection area or one-dimensional sensor. In the case of an FF-OCT application, a two-dimensional sensor may be used in a conventional manner.

During operation, interference is created in the detection area of the detector 128 between light from the reference arm and light backscattered by the sample illuminated in the illumination pattern, optionally, and in a known manner, with modulation of the path difference between the reference arm and the object arm of the sample, so as to form tomographic images, in particular front-on images.

A processing unit (not shown) receives, in a known manner, detection signals generated by the detector 128 and resulting from the detection of interference, and is configured to reconstruct microscopic images from the detection signals, for example 2D sectional images (B-scan or C-scan). The processing unit may be connected to a storage unit (not shown) for storing the generated images and/or videos. The processing unit is connected to the processing module 130 configured to generate, from the tomographic images, a tissue map at a given number of points of said detection pattern on the basis of at least one biological tissue characterization parameter, as will be explained in more detail below.

Such a microscopic analysis device 120 thus operates like an optical coherence tomography microscopy path known from the prior art.

Although one particular example is shown in FIG. 2, those skilled in the art will understand that the characterization system according to the present description applies to any known assembly from the prior art for optical coherence tomography microscopy, the optomechanical elements shown in FIG. 2 being able to be adapted accordingly or more generally to any known assembly for microscopic analysis of biological tissue.

FIG. 3A shows a diagram illustrating, in simplified form, the implementation of steps of a method for characterizing a region of interest ROI of a biological tissue S, around a suspect region 350, for example a suspect region visible on the skin, by way of a characterization system 300 according to the present description.

As in the previous examples, the characterization system 300 generally comprises a sighting device 110 and a microscopic analysis device 120, the wide-field imaging device of the sighting device 110 comprising, in this example, the microscope objective 125 of the microscopic analysis device, and the sighting and microscopic analysis paths being separated by the splitter element 113.

In this example, at least some of the elements of the sighting device and of the microscopic analysis device, including the microscope objective 125, are contained within a common mount 301 equipped with a handle 302 and referred to as a "probe" in the description. As previously, it is possible to define a distal end of such a probe that is intended to come into contact with or close to the tissue that it is sought to characterize, for example skin.

During operation, the sighting device 110 makes it possible to successively acquire reflection images of elementary surfaces 311 or "sighting images" of said region of interest ROI of the biological tissue S, the elementary surface images being acquired successively and possibly having a partial overlap in some exemplary embodiments.

For each sighting image of a plurality of said sighting images thus acquired, microscopic analysis of the biological tissue at the level of the sighting image is carried out by way of the microscopic analysis device 120. As described above, the microscopic analysis comprises illuminating the biological tissue, for example through the microscope objective, in a first given illumination pattern included in said elementary surface and detecting, in a detection pattern 321 included in said elementary surface, a light beam emitted by the biological tissue in response to said illumination of the biological tissue so as to produce microscopic analysis information, for example an image (not shown in FIG. 3A).

The characterization method then comprises processing said microscopic analysis information in order to determine, for each sighting image, at least one first biological tissue characterization parameter at a given number of points of said detection pattern.

The characterization parameter is for example, and without limitation: a morphological measurement (for example presence of cellular and tissue structures in various layers of the tissue, thickness of one or more layers of the tissue), a cytological measurement (for example density of cell nuclei, for example density of keratinocyte nuclei, or collagen anisotropy), an optical measurement (optical density, fluorescence measurement, multi-photon measurement), a chemical measurement (Raman measurement, spectroscopic measurement), a mechanical measurement (for example elastography), or a combination of these measurements.

The characterization parameter may also comprise a score based for example on one or more of the abovementioned measurements, possibly with a weighting. For example, such a score may express the presence or absence of a lesion within the tissue, in binary or non-binary form (for example via a probability percentage, a number on a given scale or a binary result). Thus, by way of example, in the example of FIG. 3A, the characterization parameter expresses the presence 332 or absence 331 of a lesion within the tissue.

The definition of the characterization parameter may also result, according to some examples, in the detection of an identical property at multiple different depths. For example, one characterization parameter may be "more than 70% probability of a lesion, measured at a depth greater than 100 µm".

It should be noted that the decision regarding presence/absence of a lesion or the probability percentage may be generated by artificial intelligence, by way of an artificial intelligence module, for example based on a deep learning model using neural networks.

Generally speaking, such an artificial intelligence module may be used to determine a characterization parameter on the basis of one or a combination of the abovementioned measurements.

Thus, in some exemplary embodiments, a deep learning model, based on neural networks, may be used on sectional images (B-scans or C-scans) to detect the presence of a pathology, for example basal cell carcinoma (BCC), with a score between 0 and 1. All of these scores, visualized front-on, form a map of pathological zones and healthy zones. A precise boundary may be computed using a threshold delimiting at-risk zones.

In one exemplary embodiment, a Microsoft®-developed ResNet-18 model with a binary output is trained to predict the presence or absence of BCC in vertical sectional images (B-scans). The model is used to predict a detection score at 0 and 1 in each 3D image. In order to limit risks of underestimating the lesion, a threshold may be used to define pathological zones. The convex envelope of this zone may be considered to be the zone to be removed for the practitioner.

In another exemplary embodiment, a Google®-developed EfficientNet-B3 model with a binary output is trained to predict the presence or absence of BCC in vertical sectional images (B-scans). The model is used to predict a detection score at 0 and 1 in each 3D image. In order to limit the surgical zone as far as possible, a threshold may be used to define pathological zones. The convex envelope of this zone may be considered to be the zone to be removed for the practitioner.

Moreover, it is entirely possible to have multiple characterization parameters at one point (if multiple characterization parameters are verified at this point), for example "more than 70% probability of a lesion" and "thickness of the epidermis less than 100 µm").

Figure 3B:
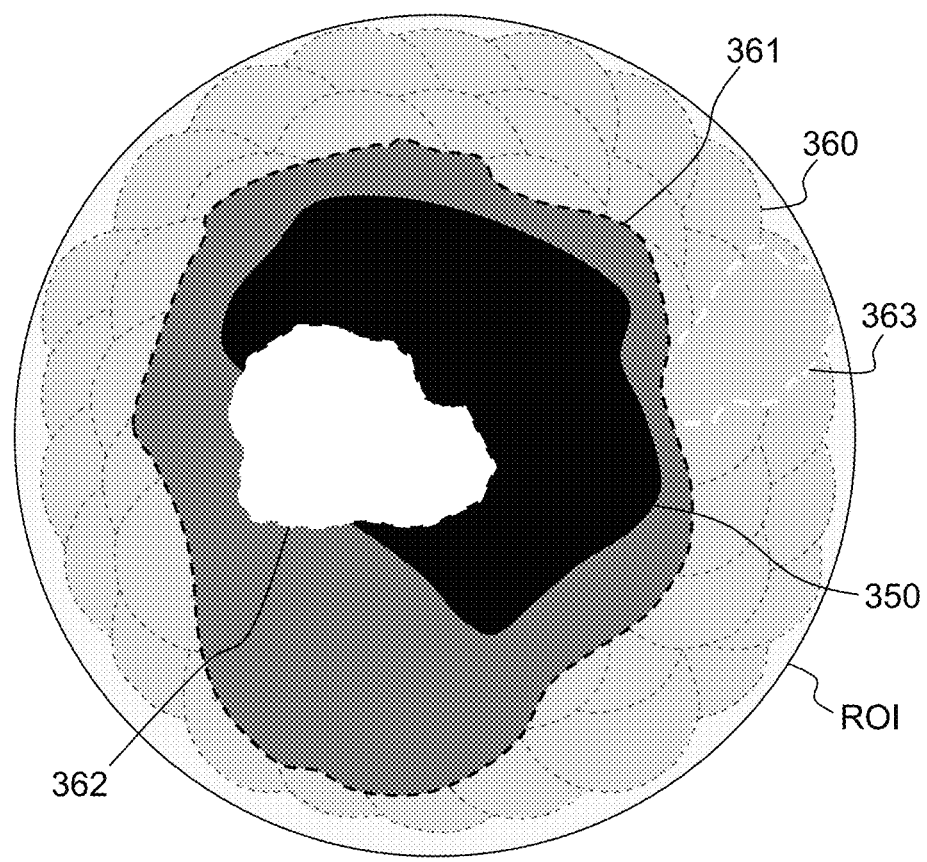
FIG. 3B shows one example of the display of a surface image of the region of interest superimposed on a map comprising a plurality of map elements respectively for various characterization parameters, obtained by way of one example of a method according to the present description.

FIG. 3B thus illustrates a first example of the display of a surface image 360 of the region of interest ROI obtained using a method according to the present description, on which the suspect region 350 is visible. Some examples of methods are described in more detail by way of FIG. 4A, 4B and FIG. 6A, 6B. Superimposed on the surface image 360, it is possible to see a first map element 361 for a first characterization parameter, a second map element 362 for a second characterization parameter and a third map element 363 for a third characterization parameter.

It should be noted that, in some exemplary embodiments, the surface image of the region of interest (not shown in the figures) may be an image obtained by mosaicking sighting images, or may be obtained by way of another, independent imaging system. Such another surface image of the region of interest is for example a dermoscopic image obtained by a dermatoscope.

It should also be noted that, in the case in particular where the surface image of the region of interest is obtained by mosaicking sighting images, the map element or said map elements may be superimposed on another surface image obtained by way of another imaging system, and localized relative to the surface image of the ROI obtained by mosaicking.

Figure 3C:
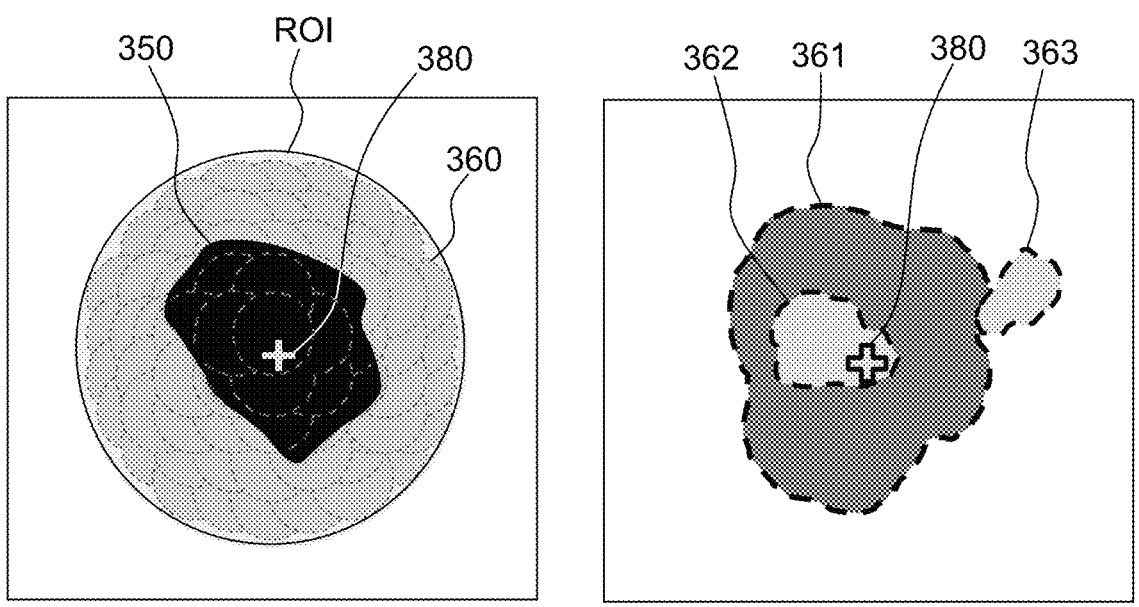
FIG. 3C shows one example of the display of a surface image of the region of interest juxtaposed with a map comprising a plurality of map elements respectively for various characterization parameters, obtained by way of one example of a method according to the present description.

FIG. 3C illustrates a second example of the display of a surface image 360 of the region of interest ROI obtained using a method according to the present description, on which the suspect region 350 is visible.

In this example, the display module is configured such that the tissue map according to one or more parameters is displayed in a manner juxtaposed with said surface image of the region of interest. The display module is then configured to additionally show a common cursor 380 in said tissue map and in said surface image of the region of interest. The common cursor may be a graphical element configured to localize the same spatial position on the map and on the surface image of the region of interest.

As previously, the surface image of the region of interest may be an image obtained by mosaicking sighting images or a surface image obtained by an independent system, for example a dermoscopic image.

Figure 4A:
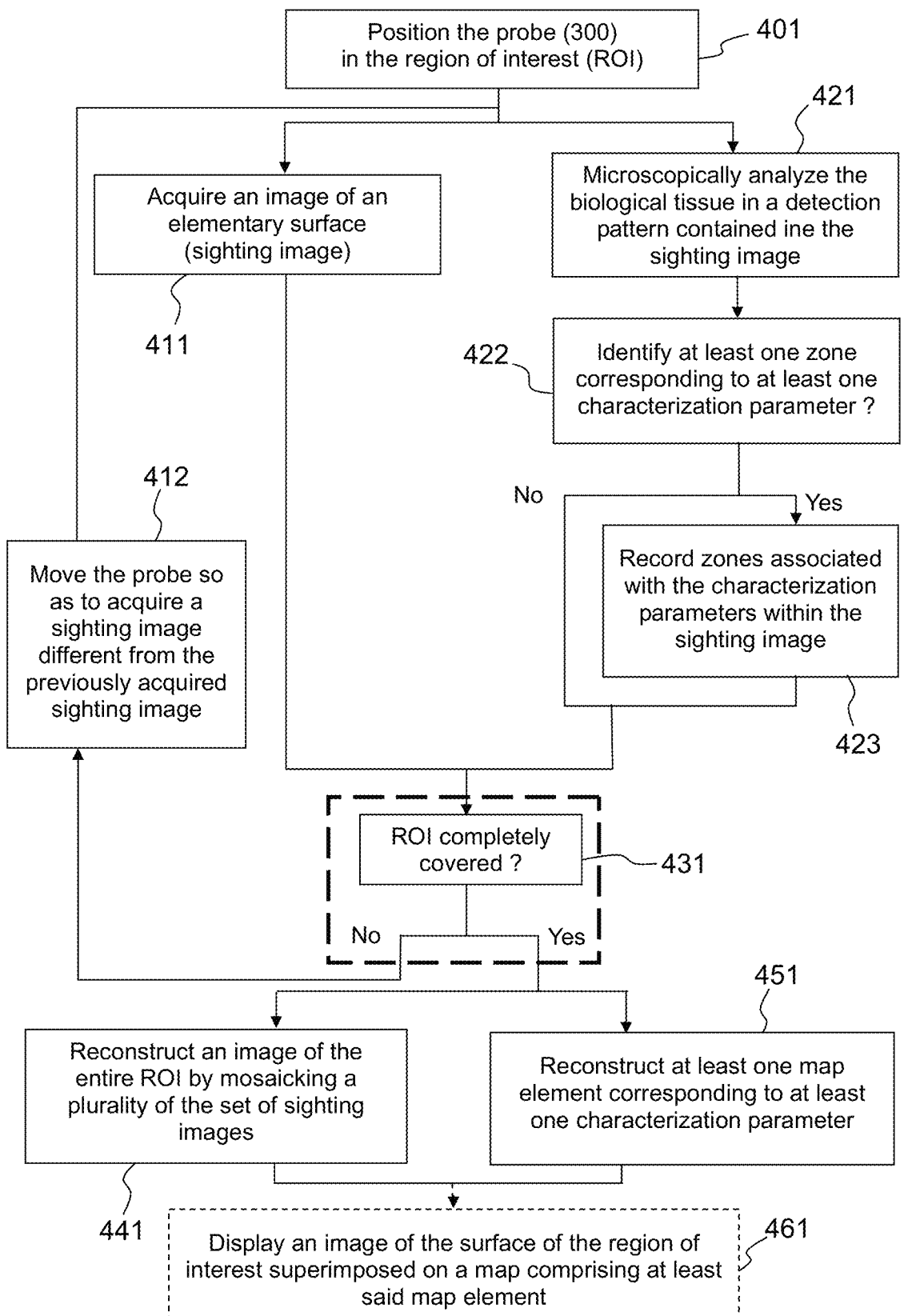
FIG. 4A shows a diagram showing a block diagram of a method according to the present description, according to a first example.
Figure 5A:
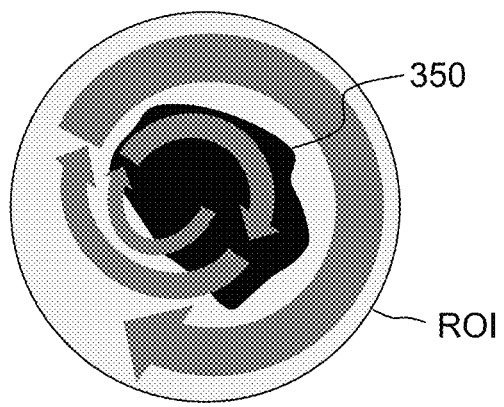
FIG. 5A shows a diagram illustrating a step of a characterization method as described in FIG. 4A.
Figure 5B:
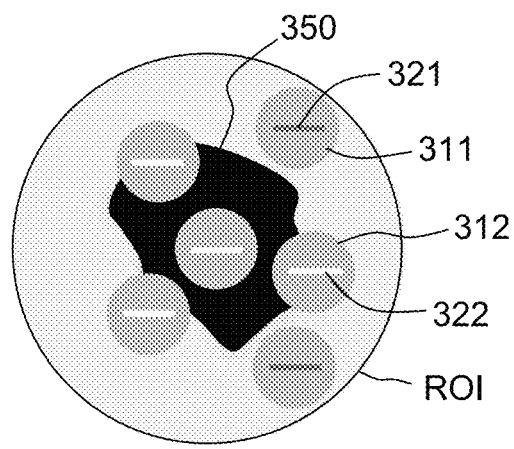
FIG. 5B shows a diagram illustrating a step of a characterization method as described in FIG. 4A.
Figure 5C:
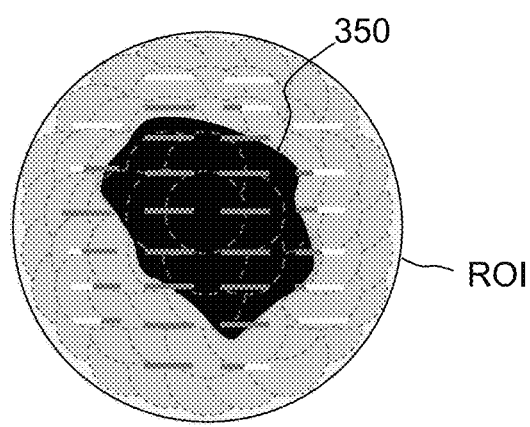
FIG. 5C shows a diagram illustrating a step of a characterization method as described in FIG. 4A.

FIG. 4A illustrates, in detail, a diagram showing a block diagram of a first example of a characterization method according to the present description, in particular for implementing the method in an in vivo characterization of biological tissue. The method is implemented for example with a characterization system of the type described with reference to the previous figures. FIG. 5A, FIG. 5B and FIG. 5C illustrate steps of a method as described in FIG. 4A. As illustrated in FIG. 3A, in the case where the characterization system forms a probe 300 able to be manipulated by an operator, for example in the context of an in vivo characterization, the method comprises a step 401 of positioning the probe 300 in the region of interest ROI of the biological tissue S that it is sought to characterize. Of course, in an ex vivo characterization, a relative displacement of the characterization system and of the sample may also be carried out by displacing the sample.

The method then comprises successively acquiring 411, 412 reflection images of elementary surfaces of said region of interest of the biological tissue, by way of a sighting device as described above and comprising a two-dimensional detector and a full-field imaging device, the successively acquired elementary surface images having a partial overlap.

For example, as illustrated in FIG. 4A, the method comprises (step 411) acquiring and displaying, by way of a display module, a first image of an elementary surface, referred to as a "sighting image" in the present description. Next, if the region of interest has not been completely covered (step 431), the operator may move the probe (412) so as to image an elementary surface different from the elementary surface previously imaged by the sighting device.

As illustrated in FIG. 5A, the displacement may take place starting from the suspect region 350 visible to the practitioner, and then moving away from the region 350 so as to cover the entire region ROI.

As illustrated in FIG. 4A, for each image of an elementary surface of a plurality of said elementary surface images thus acquired, microscopic analysis of the biological tissue 421 is carried out at the level of said elementary surface, by way of a microscopic analysis device as described above. The microscopic analysis comprises in particular illuminating the biological tissue in a first given illumination pattern included in said elementary surface, and detecting, in a detection pattern included in said elementary surface, a light beam emitted by the biological tissue in response to said illumination of the biological tissue so as to produce microscopic analysis information.

The method then comprises processing the microscopic analysis information so as to determine, from said microscopic analysis information, at least one first biological tissue characterization parameter at a given number of points of said detection pattern and produce a map element for the characterization parameter. As illustrated in FIG. 4A, this step may, more specifically, comprise an analysis step 422 in which it is sought to identify at least one detection zone of the detection pattern for which the microscopic analysis information corresponds to at least one characterization parameter. If this is the case, the one or more zones are recorded (step 423) within the corresponding sighting image.

FIG. 5B thus illustrates for example a plurality of sighting images (see for example 311, 312) for which the detection pattern is a detection line, indicated by 321, 322, respectively. The white and gray areas respectively represent different characterization parameters. The method then comprises, in this example, combination by mosaicking 441 the surface images of the plurality of surface images so as to obtain a surface image of the region of interest. The combination by mosaicking may be carried out using a known technique, comprising, for example, a registration step and a stitching step, such techniques being described for example in the Article by J. Ogien et al. [Ref. 6].

FIG. 5C thus illustrates a surface image of the region of interest resulting from the combination by mosaicking of sighting images.

Moreover, at least one map element corresponding to at least one parameter is reconstructed (step 451) from the recorded areas for at least a plurality of the sighting images.

It is then possible to display (step 461) the surface image of the region of interest and a map comprising at least said map element, said map being localized in said surface image, as shown in FIG. 3B or in FIG. 3C.

Figure 5D:
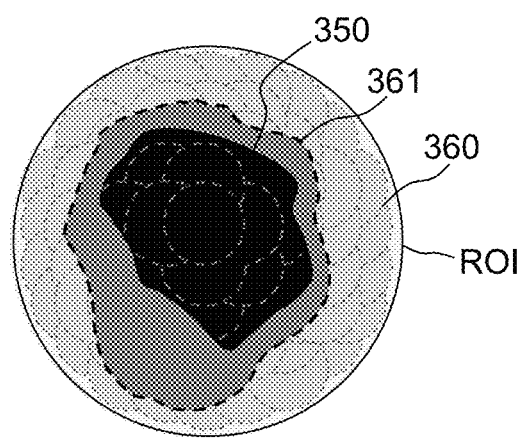
FIG. 5D shows a diagram illustrating a step of a characterization method as described in FIG. 4A.

FIG. 5D thus schematically shows the surface image 360 of the region of interest ROI, on which there is superimposed a map element 361 corresponding for example to the region identified as "having a lesion", based on the microscopic analysis information in each sighting image.

Figure 4B:
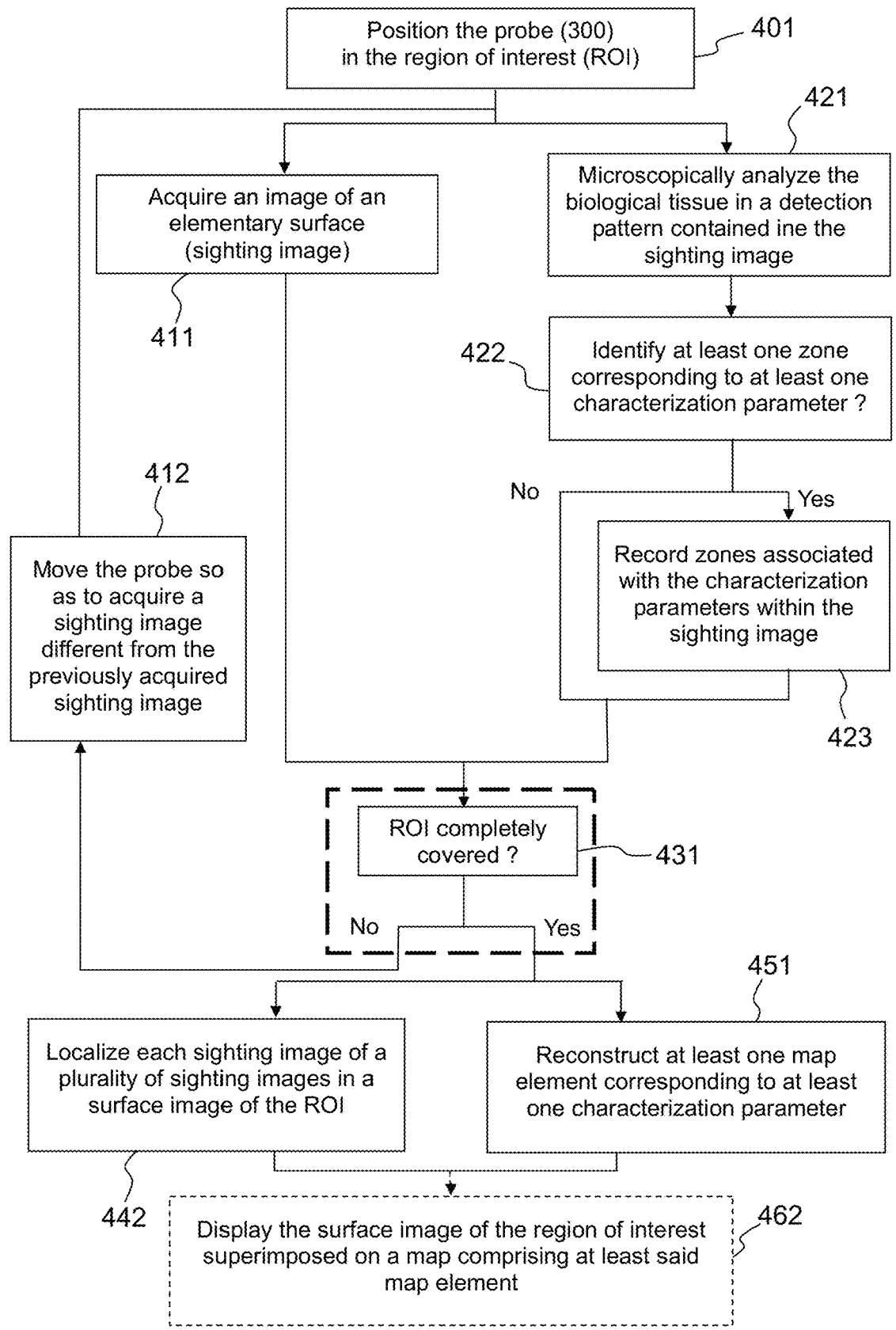
FIG. 4B shows a diagram showing a block diagram of a method according to the present description, according to a second example.

FIG. 4B illustrates a diagram showing a block diagram of a second example of a characterization method according to the present description.

In this example, steps similar to those illustrated by way of FIG. 4A are identified by the same references.

In this example, the method no longer necessarily comprises a step of mosaicking sighting images. The method here comprises a step 442 of localizing each sighting image of a plurality of sighting images in a surface image of the region of interest. This surface image of the region of interest may be an image obtained by mosaicking. It may also be an image obtained by an independent system, for example a dermoscopic image obtained by a dermatoscope. A step 462 may then comprise displaying the surface image of the region of interest superimposed on a map comprising at least said map element.

Figure 6A:
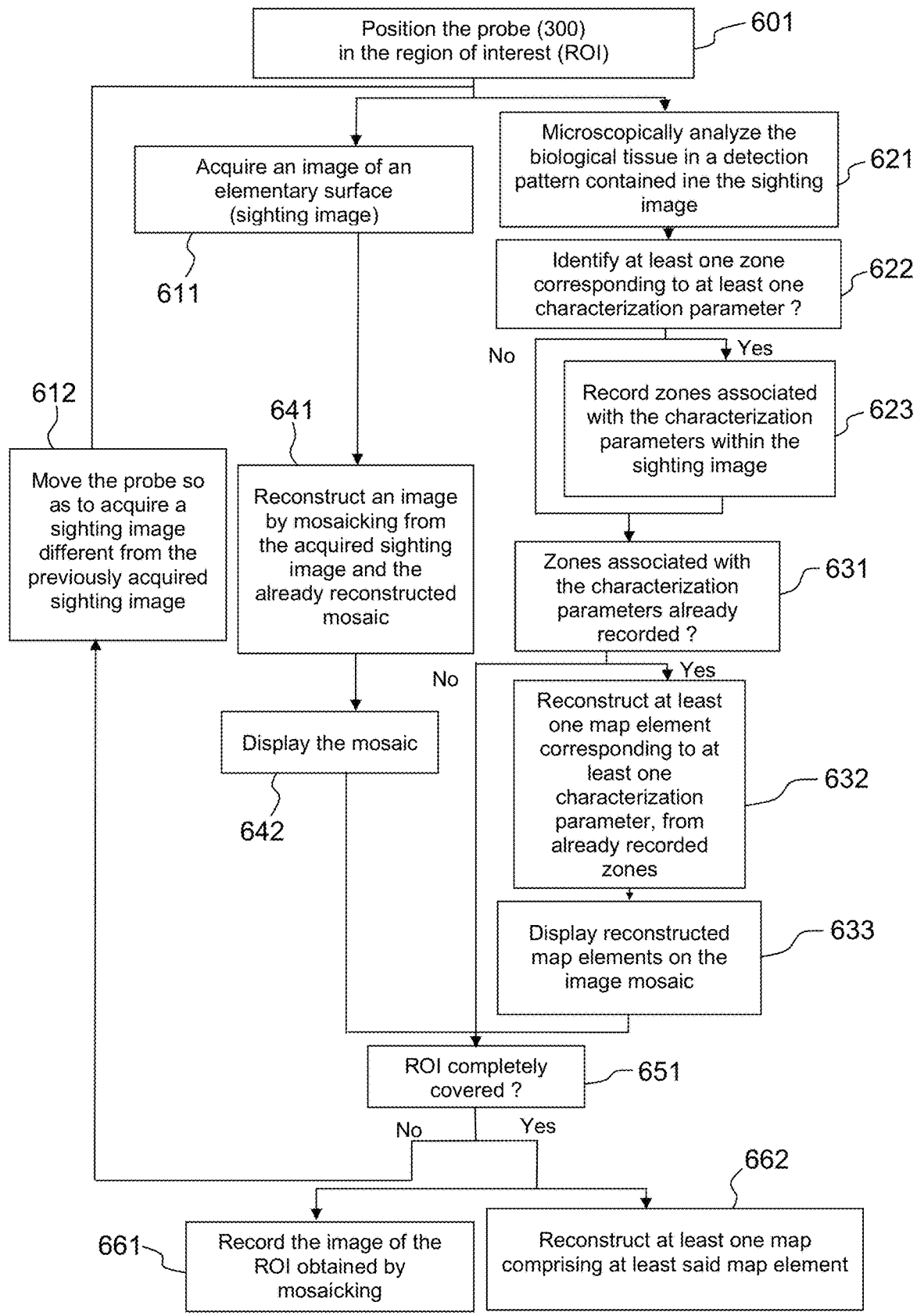
FIG. 6A shows a diagram showing a block diagram of a method according to the present description, according to a third example.

FIG. 6A illustrates, in detail, a diagram showing a block diagram of a third example of a characterization method according to the present description.

The method comprises, as previously, a step 601 of positioning the probe in the region of interest of the biological tissue that it is sought to characterize.

The method then comprises successively acquiring 611, 612 reflection images of elementary surfaces of said region of interest of the biological tissue, by way of a sighting device comprising a two-dimensional detector and a full-field imaging device, as described above, the successively acquired elementary surface images having a partial overlap.

In this example, however, the method comprises, after each step 611 of an image of an elementary surface or "sighting image", reconstructing 641 an image by mosaicking from the acquired sighting image and from the mosaic reconstructed until that point during the method and displaying 642 the image mosaic. As previously, the mosaicking is carried out using known techniques, such as those described for example in [Ref. 6].

Next, if the region of interest has not been completely covered (step 651), the operator may move the probe (612) so as to image an elementary surface different from the elementary surface previously imaged by the sighting device.

As illustrated in FIG. 6A, for each image of an elementary surface of a plurality of said acquired elementary surface images, microscopic analysis 621 of the biological tissue is carried out at the level of said elementary surface, by way of a microscopic analysis device as described above. The microscopic analysis comprises in particular illuminating the biological tissue in a first given illumination pattern included in said elementary surface, and detecting, in a detection pattern included in said elementary surface, a light beam emitted by the biological tissue in response to said illumination of the biological tissue so as to produce microscopic analysis information.

The method then comprises processing the microscopic analysis information so as to determine, from said microscopic analysis information, at least one first biological tissue characterization parameter at a given number of points of said detection pattern and produce a map element for the characterization parameter from a plurality of the sighting images. As illustrated in FIG. 6A, this step may, more specifically, comprise an analysis step 622 in which it is sought to identify at least one detection zone of the detection pattern for which the microscopic analysis information corresponds to at least one characterization parameter. If this is the case, the one or more zones are recorded (step 623) within the corresponding sighting image.

In the example of a method illustrated in FIG. 6A, at least one map element corresponding to at least one parameter is reconstructed from the recorded zones for a plurality of sighting images.

In this example, however, the method comprises, more specifically, in the case 631 where zones associated with the characterization parameters have already been recorded, a step 632 of reconstructing at least one map element corresponding to at least one characterization parameter from said recorded zones.

The method furthermore comprises (step 633) displaying the one or more map elements thus reconstructed, for example in a manner superimposed on the mosaic of images or, alternatively, in a juxtaposed manner, as described above. A user thus sees, during the characterization method, the mosaic of images forming and growing as new sighting images are acquired, and, superimposed on or juxtaposed with the mosaic, the one or more map elements.

It is thus possible for a practitioner to have an overview of the acquisition and therefore to better localize themselves for example relative to a large-field image previously acquired by dermoscopy, for example. In addition, this configuration potentially also allows the map to be displayed in real time, and therefore allows the practitioner to make decisions based on the map during the acquisition (for example to go off in a particular direction during the acquisition, or else to stop in order to directly extract part of the tissue based on the information provided by the map).

When the entire region has been covered (step 651), the image of the region of interest obtained by mosaicking during the method is recorded (step 661) and at least one map corresponding to at least one characterization parameter is reconstructed (step 662) from the map elements recorded during the method.

Figure 6B:
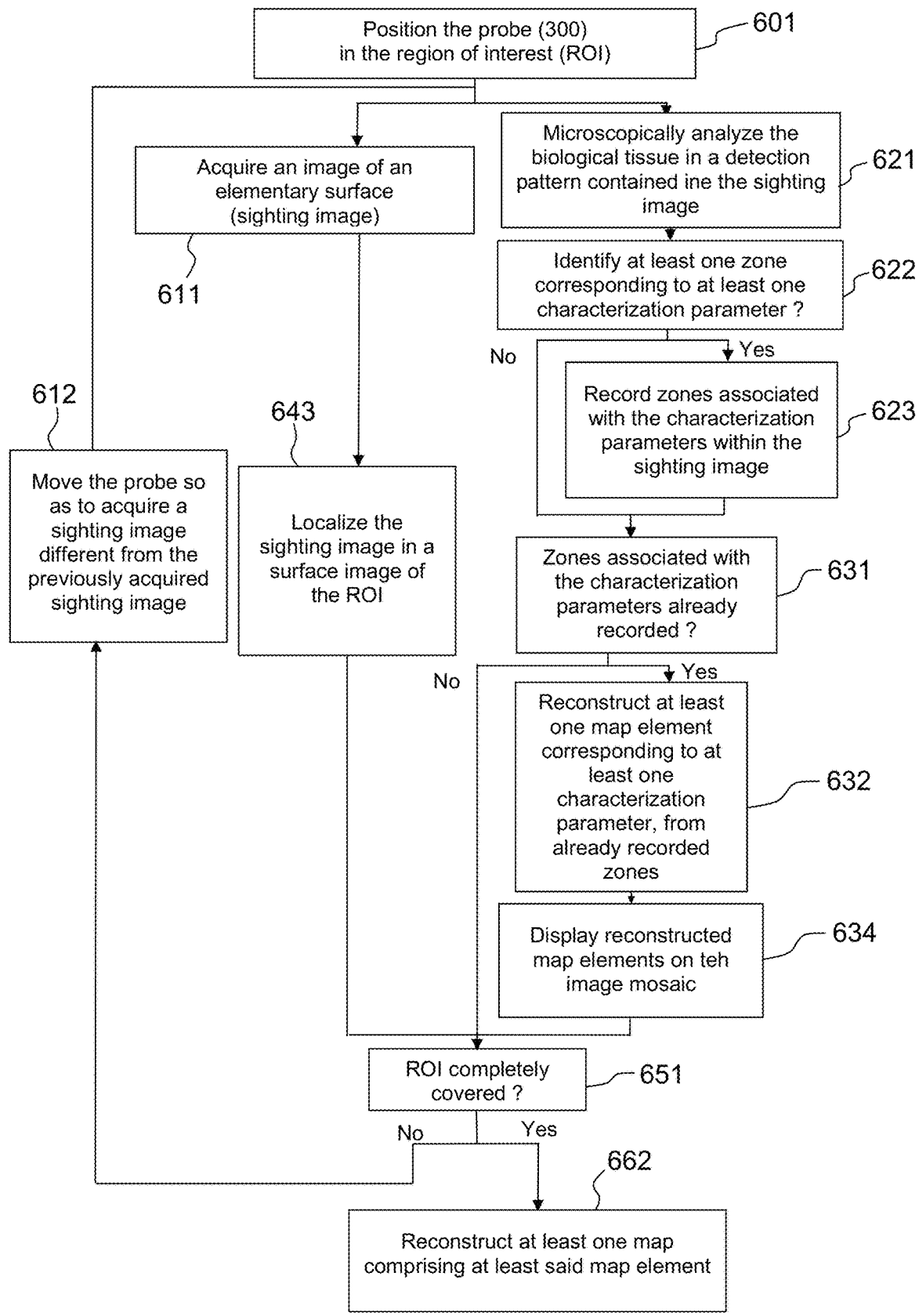
FIG. 6B shows a diagram showing a block diagram of a method according to the present description, according to a fourth example.

FIG. 6B illustrates a diagram showing a block diagram of a fourth example of a characterization method according to the present description.

In this example, steps similar to those illustrated by way of FIG. 6A are identified by the same references.

In this example, the method no longer necessarily comprises a step of mosaicking sighting images. The method here comprises a step 643 of localizing the sighting image in a surface image of the region of interest. This surface image of the region of interest may be an image obtained by an independent system, for example a dermoscopic image obtained by a dermatoscope. A step 634 may comprise displaying the reconstructed map elements on the surface image of the region of interest.

Although they have been described through a certain number of exemplary embodiments, the systems and methods for characterizing a region of interest of a biological tissue according to the present description comprise various variants, modifications and improvements that will be readily apparent to those skilled in the art, it being understood that these various variants, modifications and improvements form part of the scope of the invention as defined by the following claims.

REFERENCES

Ref. 1: A. Alfonso-Garcia et al. "*Real-time augmented reality for delineation of surgical margins during neurosurgery using autofluorescence lifetime contrast*", J Biophotonics, 2020 January; 13(1): e201900108

Ref 2: WO2020087164

Ref 3: S. Li, "*A review of feature detection and match algorithms for localization and mapping*", IOP Conference Series: Materials Science and Engineering vol. 231 012003 (2017)

Ref 4: Published patent application WO2015092019

Ref 5: E. Beaurepaire et al. "*Full-field optical coherence microscopy*" Opt. Lett. 23, 244-246 (1998)

Ref 6: Ogien et al., "*Video-mosaicking of human skin in vivo using handheld line-field confocal optical coherence tomography*" Proc. SPIE 11211, Photonics in Dermatology and Plastic Surgery 2020, 1121114 (19 Feb. 2020)

Ref. 7: WO2022017784

The invention claimed is:

1. A system for characterizing a region of interest of a biological tissue, comprising:
   a sighting device comprising:
      a full-field illumination device configured to illuminate the biological tissue in a first spectral band;
      a two-dimensional detector comprising a detection area; and
      a full-field imaging device comprising a first optical axis and configured to produce a first surface image of a first surface among a plurality of surfaces in the region of interest of the biological tissue on said detection area of the two-dimensional detector;
   a microscopic analysis device comprising:
      a microscope objective comprising a second optical axis, wherein the full-field imaging device and the microscope objective are fixed with a common mount;
      an illumination path configured to illuminate the first surface of the biological tissue using a second spectral band; and
      a detection path comprising said microscope objective, said detection path being configured to detect, a light beam emitted by the biological tissue in the first surface in response to said illumination of the biological tissue and generate microscopic analysis information;
   a data processing unit comprising:
      a first processing module configured to determine, from said microscopic analysis information, at least one first biological tissue characterization parameter at a given number of points of the biological tissue; and
      a second processing module configured to
         obtain a plurality of surface images that are acquired successively by moving the full-field imaging device of the sighting device among the plurality of surfaces, wherein said plurality of surface images partially overlap with each other;
         produce at least one first map element for said at least one first biological tissue characterization parameter, from said at least one first biological tissue characterization parameter determined using the first processing module for at least some of the plurality of surface images, and
         produce a second surface image of the region of interest by mosaicking said plurality of surface images; and
      a display module configured to display a tissue map comprising at least said first map element, said tissue map being localized relative to said second surface image of the region of interest.

2. The system as claimed in claim 1, wherein the display module is configured to additionally display said second surface image of the region of interest or a third surface image of the entire region of interest acquired by another imaging system and localized relative to said second surface image of the region of interest.

3. The system as claimed in claim 2, wherein the display module is configured to display said tissue map in a manner superimposed on said second surface image of the region of interest or on said third surface image of the entire region of interest.

4. The system as claimed in claim 2, wherein the display module is configured such that said tissue map is displayed in a manner juxtaposed with said second surface image of the region of interest or with said third surface image of the entire region of interest, the display module being configured to additionally show a common cursor in said tissue map and in said second surface image of the region of interest or in said tissue map and in said third surface image of the entire region of interest.

5. The system as claimed in claim 1, wherein the full-field imaging device of the sighting device comprises said microscope objective.

6. The system as claimed in claim 1, wherein said at least one first biological tissue characterization parameter comprises a parameter chosen from among: a morphological measurement, a cytological measurement, an optical measurement, a measurement characterizing a chemical composition, a mechanical measurement, a combination of these measurements.

7. The system as claimed in claim 1, wherein said first module for processing said microscopic analysis information comprises an artificial intelligence module based on a deep learning model using neural networks.

8. The system as claimed in claim 1, wherein said microscopic analysis device is configured for confocal imaging and/or optical coherence tomography imaging and said biological tissue microscopic analysis information comprises at least one image of the biological tissue.

9. The system as claimed in claim 1, wherein said microscopic analysis device is configured for spectroscopic analysis and said biological tissue microscopic analysis information comprises at least one spectrum of said light beam emitted by the biological tissue.

10. The system as claimed in claim 1, wherein the second processing module is further configured to determine, based on said at least one first map element, a plurality of excision margins of a region of said biological tissue to be extracted, wherein the plurality of excision margins are contours of a spatial extent surrounding the region of said biological tissue.

11. A nontransitory computer readable medium comprising a computer program product comprising program code instructions for implementing a data processing method with a view to characterizing a region of interest of a biological tissue when said program is executed on a computer, the data being obtained by way of a characterization system comprising:
a sighting device comprising:
a full-field illumination device configured to illuminate the biological tissue in a first spectral band;
a two-dimensional detector comprising a detection area; and
a full-field imaging device comprising a first optical axis and configured to produce a first surface image of a first surface among a plurality of surfaces in the region of interest of the biological tissue on said detection area of the two-dimensional detector; and
a microscopic analysis device comprising:
a microscope objective comprising a second optical axis, wherein the full-field imaging device and the microscope objective are fixed with a common mount;
an illumination path configured to illuminate the first surface of the biological tissue using a second spectral band; and
a detection path comprising said microscope objective, said detection path being configured to detect a light beam emitted by the biological tissue in the first surface in response to said illumination of the biological tissue and generate microscopic analysis information;
the data processing method comprising:
determining, from said microscopic analysis information, said at least one first biological tissue characterization parameter at a given number of points of the biological tissue;
obtaining a plurality of surface images that are acquired successively by moving the full-field imaging device of the sighting device among the plurality of surfaces in the region of interest, wherein the plurality of surface images partially overlap with each other;
producing at least one first map element for said at least one first biological tissue characterization parameter, from said at least one first biological tissue characterization parameter determined for at least some of the plurality of surface images; and
producing a second surface image of the region of interest by mosaicking said plurality of surface images.

12. The nontransitory computer readable medium as claimed in claim 11, wherein said at least one first biological tissue characterization parameter is determined by way of an artificial intelligence module based on a deep learning model using neural networks.

13. A system for characterizing a region of interest of a biological tissue, comprising:
a sighting device comprising:
a full-field illumination device configured to illuminate the biological tissue in a first spectral band;
a two-dimensional detector comprising a detection area; and
a full-field imaging device comprising a first optical axis and configured to produce a first surface image of a first surface among a plurality of surfaces in the region of interest of the biological tissue on said detection area of the two-dimensional detector;
a microscopic analysis device comprising:
a microscope objective comprising a second optical axis, wherein the full-field imaging device and the microscope objective are fixed with a common mount;
an illumination path configured to illuminate the first surface of the biological tissue using a second spectral band; and
a detection path comprising said microscope objective, said detection path being configured to detect a light beam emitted by the biological tissue in the first surface in response to said illumination of the biological tissue and generate microscopic analysis information;
a data processing unit comprising:
a first processing module configured to determine, from said microscopic analysis information, at least one first biological tissue characterization parameter at a given number of points of the biological tissue; and
a second processing module configured to
obtain a plurality of surface images that are acquired successively by moving the full-field imaging device of the sighting device among the plurality of surfaces,
determining a position of each surface image of the plurality of surface images in a second image of the region of interest, wherein said second image of the region of interest is produced by way of an imaging system independent of said system for characterizing the region of interest, and
produce at least one first map element for said at least one first biological tissue characterization parameter, from said at least one first biological tissue characterization parameter determined using the first processing module for at least some of the plurality of surface images; and
a display module configured to display a tissue map comprising at least said first map element, said tissue map being localized relative to said second image of the region of interest.

14. A nontransitory computer readable medium comprising a computer program product comprising program code instructions for implementing a data processing method with a view to characterizing a region of interest of a biological tissue when said program is executed on a computer, the data being obtained by way of a characterization system comprising:
a sighting device comprising:
a full-field illumination device configured to illuminate the biological tissue in a first spectral band;
a two-dimensional detector comprising a detection area; and a full-field imaging device comprising a first optical axis and configured to produce a first surface image of a first surface among a plurality of surfaces in the region of interest of the biological tissue on said detection area of the two-dimensional detector; and a microscopic analysis device comprising:

a microscope objective comprising a second optical axis, wherein the full-field imaging device and the microscope objective are fixed with a common mount;

an illumination path configured to illuminate the first surface of the biological tissue using a second spectral band; and a detection path comprising said microscope objective, said detection path being configured to detect a light beam emitted by the biological tissue in the first surface in response to said illumination of the biological tissue and generate microscopic analysis information;

the data processing method comprising:

determining, from said microscopic analysis information, at least one first biological tissue characterization parameter at a given number of points of the biological tissue;

obtaining a plurality of surface images that are acquired successively by moving the full-field imaging device of the sighting device among the plurality of surfaces, determining a position of each surface image of the plurality of surface images in a second image of the region of interest, wherein said second image of the region of interest is produced by way of an imaging system independent of said system for characterizing the region of interest; and producing at least one first map element for said at least one first biological tissue characterization parameter, from said at least one first biological tissue characterization parameter determined for at least some of the plurality of surface images.

* * * * *